US007553928B2

(12) United States Patent
Sim et al.

(10) Patent No.: US 7,553,928 B2
(45) Date of Patent: Jun. 30, 2009

(54) USE OF DES-ASPARTATE-ANGIOTENSIN I AS AN AGENT FOR THE TREATMENT AND PREVENTION OF GLOMERULOSCLEROSIS AND RENAL FAILURE

(75) Inventors: Meng Kwoon Sim, Singapore (SG); Chorh Chuan Tan, Singapore (SG)

(73) Assignee: National University of Singapore, Singapore (SG)

( * ) Notice: Subject to any disclaimer, the term of this patent is extended or adjusted under 35 U.S.C. 154(b) by 204 days.

(21) Appl. No.: 10/269,458

(22) Filed: Oct. 11, 2002

(65) Prior Publication Data

US 2003/0086920 A1 May 8, 2003

Related U.S. Application Data

(63) Continuation of application No. PCT/SG01/00061, filed on Apr. 12, 2001.

(30) Foreign Application Priority Data

Apr. 13, 2000 (SG) .............................. 200002037-0

(51) Int. Cl.
*A61K 38/00* (2006.01)
(52) U.S. Cl. .......................... 530/316; 514/15; 530/328; 435/369
(58) Field of Classification Search ........................ None
See application file for complete search history.

(56) References Cited

U.S. PATENT DOCUMENTS

| 5,773,415 | A | | 6/1998 | Sim .............................. 514/15 |
| 5,854,388 | A | * | 12/1998 | Harding et al. .............. 530/329 |
| 6,100,237 | A | | 8/2000 | Sim .............................. 514/15 |
| 2004/0265882 | A1 | * | 12/2004 | McGrail et al. ................. 435/6 |

FOREIGN PATENT DOCUMENTS

WO    WO 99/40106    *    8/1999

OTHER PUBLICATIONS

The Kidney Disease Dictionary, American Kidney Fund, pp. 1-12, pttp://www.kidneyfund.org/facts_dictionary.asp, printed Sep. 26, 2005.*
Schieppati, et al., Chronic renal diseases as a public health problem: Epidemiology, social, and economic implications, Kidney International, 2005, vol. 68, Supplement 98, pp. S7-S10.*
Bello, et al., Prevention of chronic kidney disease: A global challenge, Kidney International , vol. 68 Supplement 98, pp. S11-S17.*
Bos, Do severe systemic sequelae of proteinuria modulate the antiproteinuria response to chronic ACE inhibition? Nephrology Dialysis Transplantation 2002, vol. 17, pp. 793-797.*
Ander, et al., Murine Models of Renal Disease: possibilties and problem in Studies Using Mutant Mice, experimental Nephrology, 2000, vol. 8, p. 181-193.*
Chen, et al., (Regulatory Peptides (2002) 106:39-46).*

Voet (D. Voet and J.G. Voet. Biochemistry, 2nd Edition.(1995), pp. 235-241).*
Rudikoff, et al., (PNAS, 1982, 79, 1979-1983).*
[Information retrieved from] http:www.neurosci.pharm.utoledo.edu/MBC3320/vasopressin.htm, 4 pages [Retrieved on Jan. 17, 2007].*
Agrawal, 2000, American Family Physician, 61, 2077-2088.*
Min, L., et al. "Effects of des-aspartate-angiotensin I on angiotensin II-induced incorporation of phenylalanine and thymidine in cultured rat cardiomyocytes and aortic smooth muscle cells,"0 *Regulatory Peptides*, 95:93-97, 2000.
Lim, B.C., et al. "Actions of des-asp-angiotensin I on the aortic rings of the normo- and hypertensive rats," *Clin. and Exper. Hypertension*, 20(1):105-117, 1998.
Sim, M.K., et al. "Determination of aminopeptidase X activity in tissues of normo- and hypertensive rats by capillary electrophoresis," *Journal of Chromatography B*, 697:259-262, 1997.
Radhakrishnan, R., et al. "Actions of D-amino acid-substituted analogues of des-Asp-angiotensin I on the central pressor action of angiotensin III," *European Journal of Pharmacology*, 294:337-339, 1995.
Sim, M.K., et al. "Effects of des-Asp-angiotensin I on experimentally-induced cardiac hypertrophy in rats," *International Journal of Cardiology*, 63:223-227, 1998.
Sim, M.K., et al. "Novel central action of des-Asp-angiotensin I," *European Journal of Pharmacology*, 257:R1-R3, 1994.
Ashton B. Morrison "Experimental Chronic Renal Insufficiency", (1966) *Meth. Achievm. exp. Path.*, vol. 1, pp. 455-475.
Blair-West et al. "The Effect of the Heptapeptide (208) and Hexapeptide (3-8) Fragments of Angiotensin II on Aldosterone Secretion", (1971) *J. Clin. Endocrinol. Metab.* 32:275.
Tsai et al. "Synthesis and Evaluation of [Des-Asp$^1$]angiotensin I as a Precursor for [Des-Asp$^1$]angiotensin II ("Angiotensin III")", (1975)*J. Med. Chem.* 18:1180.
Sim and Chai "Subtypes of losartar-sensitive angiotensin receptor in the rabbit pulmonary artery", (1996) *Br J. Pharmacol.* 117-1504.
Hamar et al., "Coinhibition of Immune and Renin-Angiotensin Systems Reduces the Pace of Glomerulosclerosis in the Rat Remnant Kidney", (1999) *J. Am. Soc. Nephrol.* 10:S234-S238.

(Continued)

*Primary Examiner*—Andrew D Kosar
*Assistant Examiner*—Satyanarayana R Gudibande
(74) *Attorney, Agent, or Firm*—Klarquist Sparkman, LLP (57) ABSTRACT

The present invention relates generally to a method for the treatment and/or prophylaxis of renal-related disorders. More particularly, the present invention contemplates a method for the treatment and/or prophylaxis of glomerulosclerosis and/or end stage renal failure and/or related conditions. The method of the present invention is preferably practised by the administration of a derivative of angiotensin I. Generally, but not exclusively, the angiotensin I derivative exhibits anti-angiotensin II properties. In a preferred embodiment, the angiotensin I is des-Aspartate-angiotensin I or a derivative, homologue or analogue thereof. The present invention further contemplates compositions for use in the treatment and/or prophylaxis of renal-related disorders such as but not limited to glomerulosclerosis and/or end stage renal failure.

8 Claims, 6 Drawing Sheets

OTHER PUBLICATIONS

Nakamura et al., "Involvement of angiotensin II in glomerulosclerosis of stroke-prone spontaneously hypertensive rats", *Kidney International*, vol. 49, Suppl. 55 (1996), pp. S-109-S-112.

Kettler et al., "Transforming Growth Factor-β and Angiotensin II: The Missing Link from Glomerular Hyperfiltration to Glomerulosclerosis", *Annu. Rev. Physiol.* 1995, 57:279-95.

Strauch et al., "Animal Models to Induce Renal Failure: A Historical Survey", *Contr. Nephrol.*, vol. 60, pp. 1-8 (Karger, Basel 1988).

Ashton B. Morrison, M.D., Ph.D., "Experimentally Induced Chronic Renal Insufficiency in the Rat", *Laboratory Investigation*, vol. 11, No. 4, 1962.

Jagger, Paul I. et al., "Hypertensive Vascular Disease," Wintrose, MW et al, editors, *Harrison's Principles of Internal Medicine, 7th* Ed., pp. 1236-1240, 1974.

* cited by examiner

USE OF DES-ASPARTATE-ANGIOTENSIN I AS AN AGENT FOR THE TREATMENT AND PREVENTION OF GLOMERULOSCLEROSIS AND RENAL FAILURE

CROSS-REFERENCE TO RELATED APPLICATION

This is a continuation of International Application No. PCT/SG01/00061, filed Apr. 12, 2001, which application is incorporated herein by reference.

TECHNICAL FIELD

1. Field of the Invention

The present invention relates generally to a method for the treatment and/or prophylaxis of renal-related disorders. More particularly, the present invention contemplates a method for the treatment and/or prophylaxis of glomerulosclerosis and/or end stage renal failure and/or related conditions. The method of the present invention is preferably practised by the administration of a derivative of angiotensin I. Generally, but not exclusively, the angiotensin I derivative exhibits anti-angiotensin II properties. In a preferred embodiment, the angiotensin I is des-Aspartate-angiotensin I or a derivative, homologue or analogue thereof. The present invention further contemplates compositions for use in the treatment and/or prophylaxis of renal-related disorders such as but not limited to glomerulosclerosis and/or end stage renal failure.

2. Background of the Invention

Renal failure and other renal related conditions contribute to significant morbidity and mortality in patients affected by such conditions. There is a need, therefore, to develop more efficacious pharmaceutical molecules useful in the treatment of renal conditions.

des-Aspartate angiotensin I (des-Asp-angiotensin I) is a nonapeptide produced from a decapeptide by the action of an aminopeptidase. The nonapeptide is produced from angiotensin I by enzymatic $NH_2$-terminal degradation (1). des-Asp-angiotensin I is a substrate for plasma and pulmonary angiotensin converting enzyme (2). Furthermore, des-Asp-angiotensin I acts on a specific indomethacin-sensitive subtype of angiotensin receptor (3) and to antagonize the pressor (4) and hypertrophic (5) actions of angiotensin II. Angiotensin II is a key mediator of glomerulosclerosis in progressive kidney diseases (6-8). In work leading up to the present invention, the inventors determined that the anti-angiotensin II properties of des-Asp-angiotensin I can be exploited in the treatment and/or prophylaxis of renal-related disorders.

SUMMARY OF THE INVENTION

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

One aspect of the present invention contemplates a method for the treatment and/or prophylaxis of a renal-related disorder, said method comprising administering to a subject an effective amount of a derivative of angiotensin I for a time and under conditions sufficient for the onset of the renal-related disorder to be prevented, inhibited or delayed or the symptoms of the renal-related disorder to be ameliorated.

Another aspect of the present invention provides a method for the treatment and/or prophylaxis of a renal-related disorder, said method comprising administering to a subject an angiotensin II-inhibiting effective amount of a derivative of angiotensin I for a time and under conditions sufficient for the onset or the renal-related disorder to be prevented, inhibited or delayed or the symptoms of the renal-related disorder to be ameliorated.

Yet another aspect of the present invention is directed to a method for the treatment and/or prophylaxis of a renal-related disorder, said method comprising administering to a subject an effective amount of des-Asp-angiotensin I or a derivative, homologue or analogue thereof for a time and under conditions sufficient for the onset of the renal-related disorder to be prevented, inhibited or delayed or the symptoms of the renal-related disorder to be ameliorated.

Still a further aspect of the present invention provides a composition for use in the treatment and/or prophylaxis of renal-related disorders, said composition comprising a derivative of angiotensin I and a pharmaceutically acceptable carrier and/or diluent.

In yet another aspect, the invention provides a method for the treatment and/or prophylaxis of a renal-related disorder selected from the group consisting of focal or segmental glomerulosclerosis, oligomeganephronia, membranous nephropathy, minimal change nephritis, proliferative glomerulonephritis, analgesic nephropathy, diabetes mellitus, unilateral nephrectomy, cortical necrosis, unilateral renal agenesis and end stage renal failure, said method comprising administering to a subject in need thereof an effective amount of a derivative of angiotensin I for a time and under conditions sufficient for the onset of the renal-related disorder to be prevented, inhibited or delayed or the symptoms of the renal-related disorder to be ameliorated, said derivative of angiotensin I inhibiting one or more activities of angiotensin II.

In yet another aspect, the invention provides a kit for the prophylaxis or treatment of a renal-related disorder comprising: a container suitable for storing a pharmaceutical preparation; an effective amount of des-Asp-angiotensin I or a derivative, homologue or analogue thereof in said container, said derivative, homologue or analogue inhibiting one or more activities of angiotensin II; and instructions associated with said container giving instructions for the use of said des-Asp-angiotensin I or a derivative, homologue or analogue thereof for the prophylaxis or treatment of a renal-related disorder selected from the group consisting of focal or segmental glomerulosclerosis, oligomeganephronia, membranous nephropathy, minimal change nephritis, proliferative glomerulonephritis, analgesic nephropathy, diabetes mellitus, unilateral nephrectomy, cortical necrosis, unilateral renal agenesis and end stage renal failure.

In yet another aspect, the invention provides use of des-Asp-angiotensin I in the manufacture of a medicament for use in the prevention or treatment of a renal-related disorder selected from the group consisting of focal or segmental glomerulosclerosis, oligomeganephronia, membranous nephropathy, minimal change nephritis, proliferative glomerulonephritis, analgesic nephropathy, diabetes mellitus, unilateral nephrectomy, cortical necrosis, unilateral renal agenesis and end stage renal failure.

DETAILED DESCRIPTION OF THE PRE EMBODIMENTS

The present invention is predicated in part on the determination that a derivative of angiotensin I prevents or otherwise attenuates or ameliorates the effects of glomerulosclerosis and the accompanying proteinuria in experimentally-induced nephropathic rats. Animal models for studying renal disease are well accepted in the art (9). In accordance with the present invention, the effect of des-Asp-angiotensin I on the proteinuria in rats which had undergone sub-total nephrectomy was determined. It was surprisingly discovered that des-Asp-angiotensin was capable of preventing or otherwise ameliorating the effects of renal-related disorders.

Accordingly, one aspect of the present invention provides a method for the prophylaxis and/or treatment of a renal-related disorder, said method comprising administering to a subject an effective amount of a derivative of angiotensin I.

More particularly, the present invention contemplates a method for the treatment and/or prophylaxis of a renal-related disorder, said method comprising administering to a subject an effective amount of a derivative of angiotensin I for a time and under conditions sufficient for the onset of the renal-related disorder to be prevented, inhibited or delayed or the symptoms of the renal-related disorder to be ameliorated.

The term renal-related disorder is used herein in its broadest sense and includes focal and segmental glomerulosclerosis, oligomeganephronia, membranous nephropathy, minimal change nephritis, proliferative glomerulonephritis, analgesic nephropathy, diabetes mellitus, unilateral nephrectomy, cortical necrosis, unilateral renal agenesis and end stage renal failure. Preferably, the renal-related disorder is glomerulosclerosis and/or end stage renal failure.

A derivative of des-Asp-angiotensin I includes any mutant, fragment, part or portion of angiotensin I or des-Asp-angiotensin I including molecules comprising single or multiple amino acid substitutions, deletions and/or additions to angiotensin I or to des-Asp-angiotensin I. Generally, the derivative of angiotensin I inhibits, reduces or otherwise interferes with the activity or functioning of angiotensin II.

According to this embodiment, there is provided a method for the treatment and/or prophylaxis of a renal-related disorder, said method comprising administering to a subject an angiotensin II-inhibiting effective amount of a derivative of angiotensin I for a time and under conditions sufficient for the onset of the renal-related disorder to be prevented, inhibited or delayed or the symptoms of the renal-related disorder to be ameliorated.

The preferred derivative in accordance with the present invention is des-Asp-angiotensin I or a derivative, homologue or analogue thereof. Reference to a homologue or an analogue includes a mimotope or peptide or analogue mimetic. Such derivatives, homologues and analogues may function in place of des-Asp-angiotensin I or its equivalent or they may act as an agonist thereof or, when necessary, an antagonist thereof.

As stated above, a derivative includes single or multiple amino acid substitutions, additions and/or deletions to des-Asp-angiotensin I.

Amino acid insertional derivatives of des-Asp-angiotensin I include amino and/or carboxyl terminal fusions as well as intra-sequence insertions of single or multiple amino acids. Insertional amino acid sequence variants are those in which one or more amino acid residues are introduced into a predetermined site in the des-Asp-angiotensin I although random insertion is also possible with suitable screening of the resulting product. Deletional variants are characterized by the removal of one or more amino acids from the sequence. Substitutional amino acid variants are those in which at least one residue in the sequence has been removed and a different residue inserted in its place.

Where the des-Asp-angiotensin I is derivatized by amino acid substitution, the amino acids are generally replaced by other amino acids having like properties, such as hydrophobicity, hydrophilicity, electronegativity, bulky side chains and the like. Amino acid substitutions are typically of single residues. Amino acid insertions will usually be in the order of about 1-6 amino acid residues and deletions will range from about 1-6 residues. Preferably, deletions or insertions are made in adjacent pairs, i.e. a deletion of two residues or insertion of two residues.

Homologues include functionally, structurally or stereochemically similar polypeptides from, for example, other sources such as for livestock animals, laboratory test animals or primates. The similar peptides may also be homologues of des-Asp-angiotensin I.

Analogues and mimetics include molecules which contain non-naturally occurring amino acids as well as molecules which do not contain amino acids but nevertheless behave functionally the same as the des-Asp-angiotensin I. Analogues contemplated herein include modifications to side chains, incorporation of unnatural amino acids and/or their derivatives during peptide synthesis and the use of crosslinkers and other methods which impose conformational constraints on the peptide molecule or their analogues.

Examples of incorporating unnatural amino acids and derivatives during peptide synthesis include, but are not limited to, use of norleucine, 4-amino butyric acid, 4-amino-3-hydroxy-5-phenylpentanoic acid, 6-aminohexanoic acid, t-butylglycine, norvaline, phenylglycine, ornithine, sarcosine, 4-amino-3-hydroxy-6-methylheptanoic acid, 2-thienyl alanine and/or D-isomers of amino acids.

Crosslinkers can be used, for example, to stabilize 3D conformations, using homo-bifunctional crosslinkers such as the bifunctional imido esters having $(CH_2)_n$ spacer groups with n=1 to n=6, glutaraldehyde, N-hydroxysuccinimide esters and hetero-bifunctional reagents which usually contain an amino-reactive moiety such as N-hydroxysuccinimide and another group specific-reactive moiety.

All these types of modifications may be important to stabilize the subject des-Asp-angiotensin I. This may be important if used, for example, in the manufacture of a vaccine or therapeutic composition or in detection assays. Examples of unnatural amino acids contemplated by the present invention are presented in Table 1.

TABLE 1

| Non-conventional amino acid | Code | Non-conventional amino acid | Code |
|---|---|---|---|
| α-aminobutyric acid | Abu | L-N-methylalanine | Nmala |
| α-amino-α-methyl-butyrate | Mgabu | L-N-methylarginine | Nmarg |
| aminocyclopropane-carboxylate | Cpro | L-N-methylasparagine | Nmasn |
|  |  | L-N-methylaspartic acid | Nmasp |
| aminoisobutyric acid | Aib | L-N-methylcysteine | Nmcys |

TABLE 1-continued

| Non-conventional amino acid | Code | Non-conventional amino acid | Code |
|---|---|---|---|
| aminonorbornyl-carboxylate | Norb | L-N-methylglutamine | Nmgln |
| | | L-N-methylglutamic acid | Nmglu |
| cyclohexylalanine | Chexa | L-N-methylhistidine | Nmhis |
| cyclopentylalanine | Cpen | L-N-methylisoleucine | Nmile |
| D-alanine | Dal | L-N-methylleucine | Nmleu |
| D-arginine | Darg | L-N-methyllysine | Nmlys |
| D-aspartic acid | Dasp | L-N-methylmethionine | Nmmet |
| D-cysteine | Dcys | L-N-methylnorleucine | Nmnle |
| D-glutamine | Dgln | L-N-methylnorvaline | Nmnva |
| D-glutamic acid | Dglu | L-N-methylornithine | Nmorn |
| D-histidine | Dhis | L-N-methylphenylalanine | Nmphe |
| D-isoleucine | Dile | L-N-methylproline | Nmpro |
| D-leucine | Dleu | L-N-methylserine | Nmser |
| D-lysine | Dlys | L-N-methylthreonine | Nmthr |
| D-methionine | Dmet | L-N-methyltryptophan | Nmtrp |
| D-ornithine | Dorn | L-N-mehyltyrosine | Nmtyr |
| D-phenylalanine | Dphe | L-N-methylvaline | Nmval |
| D-proline | Dpro | L-N-methylethylglycine | Nmetg |
| D-serine | Dser | L-N-methyl-t-butyl-glycine | Nmtbug |
| D-threonine | Dthr | L-norleucine | Nle |
| D-tryptophan | Dtrp | L-norvaline | Nva |
| D-tyrosine | Dtyr | α-methyl-aminoiso-butyrate | Maib |
| D-valine | Dval | α-methyl-α-amino-butyrate | Mgabu |
| D-α-methylalanine | Dmala | α-methylcyclohexyl-alanine | Mchexa |
| D-α-methylarginine | Dmarg | α-methylcylopentyl-alanine | Mcpen |
| D-α-methylasparagine | Dmasn | α-methyl-α-napthyl-alanine | Manap |
| D-α-methylaspartate | Dmasp | α-methylpenicillamine | Mpen |
| D-α-methylcysteine | Dmcys | N-(4-aminobutyl)glycine | Nglu |
| D-α-methylglutamine | Dmgln | N-(2-aminoethyl)glycine | Naeg |
| D-α-methylhistidine | Dmhis | N-(3-aminopropyl)glycine | Norn |
| D-α-methylisoleucine | Dmile | N-amino-α-methyl-butyrate | Nmaabu |
| D-α-methylleucine | Dmleu | α-napthylalanine | Anap |
| D-α-methyllysine | Dmlys | N-benzylglycine | Nphe |
| D-α-methylmethionine | Dmmet | N-(2-carbamylethyl)glycine | Ngln |
| D-α-methylornithine | Dmorn | N-(carbamylmethyl)glycine | Nasn |
| D-α-methylphenyl-alanine | Dmphe | N-(2-carboxyethyl)glycine | Nglu |
| D-α-methylproline | Dmpro | N-(carboxymethyl)glycine | Nasp |
| D-α-methylserine | Dmser | N-cyclobutylglycine | Ncbut |
| D-α-methylthreonine | Dmthr | N-cycloheptylglycine | Nchep |
| D-α-methyltryptophan | Dmtrp | N-cyclohexylglycine | Nchex |
| D-α-methyltyrosine | Dmty | N-cyclodecylglycine | Ncdec |
| D-α-methylvaline | Dmval | N-cylcododecylglycine | Ncdod |
| D-N-methylalanine | Dnmala | N-cyclooctylglycine | Ncoct |
| D-N-methylarginine | Dnmarg | N-cyclopropylglycine | Ncpro |
| D-N-methylasparagine | Dnmasn | N-cycloundecylglycine | Ncund |
| D-N-methylaspartate | Dnmasp | N-(2,2-diphenylethyl)glycine | Nbhm |
| D-N-methylcysteine | Dnmcys | N-(3,3-diphenylpropyl)glycine | Nbhe |
| D-N-methylglutamine | Dnmgln | N-(3-guanidinopropyl)glycine | Narg |
| D-N-methylglutamate | Dnmglu | N-(1-hydroxyethyl)glycine | Nthr |
| D-N-methylhistidine | Dnmhis | N-(hydroxyethyl))glycine | Nser |
| D-N-methylisoleucine | Dnmile | N-(imidazolylethyl))glycine | Nhis |
| D-N-methylleucine | Dnmleu | N-(3-indolylyethyl)glycine | Nhtrp |
| D-N-methyllysine | Dnmlys | N-methyl-α-amino-butyrate | Nmgabu |
| N-methylcyclohexyl-alanine | Nmchexa | D-N-methylmethionine | Dnmmet |
| D-N-methylornithine | Dnmorn | N-methylcyclopentyl-alanine | Nmcpen |
| N-methylglycine | Nala | D-N-methylphenyl-alanine | Dnmphe |
| N-methylaminoiso-butyrate | Nmaib | D-N-methylproline | Dnmpro |
| N-(1-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nval |
| D-N-methyltyrosine | Dnmtyr | N-methyla-napthyl-alanine | Nmanap |
| D-N-methylvaline | Dnmval | N-methylpenicillamine | Nmpen |
| α-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L- -methylarginine | Marg | L-α-methylasparagine | Masn |
| L- -methylaspartate | Masp | L-α-methyl-t-butyl-glycine | Mtbug |
| L- -methylcysteine | Mcys | L-methylethylglycine | Metg |
| L- -methylglutamine | Mgln | L-α-methylglutamate | Mglu |
| L- -methylhistidine | Mhis | L-α-methylhomophenyl-alanine | Mhphe |
| L- -methylisoleucine | Mile | N-(2-methylthioethyl)glycine | Nmet |
| L- -methylleucine | Mleu | L-α-methyllysine | Mlys |
| L- -methylmethionine | Mmet | L-α-methylnorleucine | Mnle |
| L- -methylnorvaline | Mnva | L-α-methylornithine | Morn |
| L- -methylphenyl-alanine | Mphe | L-α-methylproline | Mpro |
| L- -methylserine | Mser | L-α-methylthreonine | Mthr |
| L- -methyltryptophan | Mtrp | L-α-methyltyrosine | Mtyr |
| L- -methylvaline | Mval | L-N-methylhomophenyl-alanine | Nmhphe |
| N-(N-(2,2-diphenyl-ethyl)carbamyl-methyl)glycine | Nnbhm | N-(N-(3,3-diphenyl-propyl)carbamylmethyl)glycine | Nnbhe |
| 1-carboxy-1-(2,2-di-phenylethylamino)-cyclopropane | Nmbc | | |

The present invention further contemplates chemical equivalents of the des-Asp-angiotensin I. Chemical equivalents may not necessarily be derived from the subject des-Asp-angiotensin I itself but may share certain conformational or functional similarities. Alternatively, chemical equivalents may be specifically designed to mimic certain physiochemical properties of the des-Asp-angiotensin I. Chemical equivalents may be chemically synthesized or may be detected following, for example, natural product screening. Preferably, a chemical equivalent is a functional equivalent.

As mentioned above, included within the scope of the present invention are functionally-equivalent variants of des-Asp-angiotensin I and their fragments and precursors. "Functionally-equivalent" is used herein to define peptides or polypeptides related to or derived from the angiotensin I or its derivative such as des-Asp-angiotensin I where the amino acid sequence has been modified by single or multiple amino acid substitutions, addition and/or deletion and also sequences where the amino acids have been chemically modified, including by deglycosylation or glycosylation, but which nonetheless retain anti-angiotensin II activity.

Reference herein to the des-Asp-angiotensin I of the present invention should be read as including reference to all forms of this molecule including, by way of example, isoforms, monomeric, dimeric and multimeric forms and peptide fragments of the des-Asp-angiotensin I as well as homologues and functional equivalents thereof. Other functionally equivalent derivatives or homologues of angiotensin I are also encompassed by this term.

The amino acid variants referred to above may readily be made using peptide synthetic techniques well known in the art, such as solid phase peptide synthesis and the like, or by recombinant DNA manipulations. Techniques for making substitution mutations at predetermined sites in DNA having known or partially known sequence are well known and include, for example, M13 mutagenesis. The manipulation of DNA sequence to produce variant proteins which manifest as substitutional, insertional or deletional variants are conveniently described, for example, in Sambrook et al. (10).

Accordingly, another aspect of the present invention provides a method for the treatment and/or prophylaxis of a renal-related disorder, said method comprising administering to a subject an effective amount of des-Asp-angiotensin I or a derivative, homologue or analogue thereof for a time and under conditions sufficient for the onset of the renal-related disorder to be prevented, inhibited or delayed or the symptoms of the renal-related disorder to be ameliorated.

Yet a further aspect of the present invention contemplates the use of a derivative of angiotensin I in the manufacture of a medicament in the treatment and/or prophylaxis of renal-related disorders.

The present invention further provides a composition for use in the treatment and/or prophylaxis of renal-related disorders, said composition comprising a derivative of angiotensin I and a pharmaceutically acceptable carrier and/or diluent.

Preferably, the derivative of angiotensin I inhibits angiotensin II activity or all or part of the effects of angiotensin II.

Most preferably, the derivative is des-Asp-angiotensin I or a derivative, homologue or analogue thereof.

Preferably, the renal-related disorder is glomerulosclerosis and/or end stage renal failure.

According to this aspect of the present invention, an effective amount of the derivative of angiotensin I such as but not limited to des-Asp-angiotensin I or a derivative, homologue or analogue thereof or salt thereof, or a pharmaceutical composition containing the same, as described below, is administered to a subject, such as a human patient, via any acceptable method known in the art, either singly or in combination with other pharmaceutical agents such as captopril or other angiotensin converting enzyme inhibitors or angiotensin receptor antagonists. The compound or composition is administered orally, by suppository, or parenterally (e.g. intramuscularly, intravenously, subcutaneously or intradermally), and in the form of either solid or liquid dosage including tablets, suspensions, or solutions, as is discussed in more detail below. The administration may be conducted in single dosage form with continuous therapy or in single dose therapy ad libitum.

Useful pharmaceutical carriers for the preparation of the pharmaceutical compositions hereof can be solids, liquids or mixtures thereof; thus, the compositions can take the form of tablets, pills, capsules, powders, enterically coated or other protected formulations, sustained release formulations, erodible formulations, implantable devices or components thereof, microsphere formulations, solutions, suspensions, elixirs, aerosols and the like.

Water, saline, aqueous dextrose, and glycols are preferred liquid carriers, particularly (when isotonic) for injectable solutions. The carrier can be selected from various oils including those of petroleum, animal, vegetable or synthetic origin, for example, peanut oil, soybean oil, mineral oil, sesame oil, and the like. Suitable pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk, glycerol, propylene glycol, water, ethanol, and the like. The composition may be subjected to conventional pharmaceutical expedients such as sterilization and may contain conventional pharmaceutical additives such as preservatives, stabilizing agents, wetting or emulsifying agents, salts for adjusting osmotic pressure, buffers and the like. Suitable pharmaceutical carriers and their formulations are described in Martin, A Remington's Pharmaceutical Sciences, $15^{th}$ Ed.; Mack Publishing Co., Easton (1975); see, e.g. pp. 1405-1412 and pp 1461-1487. Such compositions will, in general, contain an effective amount of the active compound together with a suitable amount of carrier so as to prepare the proper dosage form for proper administration to the host.

In one preferred embodiment, the therapeutic methods of the present invention are practised when the relief of symptoms is specifically required or perhaps imminent; in another preferred embodiment, the method hereof is effectively practised as a continuous or prophylactic treatment.

In the practice of the therapeutic methods of the invention, the particular dosage of pharmaceutical composition to be administered to the subject will depend on a variety of consideration including the stage of the disease or condition, the severity thereof, the schedule of administration, the age and physical characteristics of the subject, and so forth. Proper dosages may be established using clinical approaches familiar to the medicinal arts.

Although the present invention is particularly exemplified herein in relation to rats, it is understood that the present invention extends to the use of the angiotensin derivatives in any mammal including, but not limited to, humans, mice, rabbits, livestock animals and primates.

The present invention is further described in the following non-limiting Examples.

EXAMPLE 1

Source of Materials

Des-Asp-angiotensin I was obtained from Bachem (Dubendorf, Switzerland). Des-Aspartate-angiotensin I can be prepared by techniques well known in the art. Adult Sprague Dawley rats (SD, 250-300 g) were obtained from the Animal Center, National University of Singapore.

EXAMPLE 2

Induction of Glomerulosclerosis and Proteinuria

Five-sixths nephrectomy was carried out as described by Morrison (11). Briefly, each animal was anaesthetized with 7% w/v chloral hydrate (0.4 g/kg, i.p.). An incision was made in the ventral abdominal wall to access the kidneys. Right nephrectomy was performed and the cranial and caudal third of the left kidney were cut off. Tissue adhesive (Histoccryl, B. Braun) was used to seal the cut ends of the left kidney and prevent bleeding. In this way ⅚ of the renal parenchyma was removed. This model results in focal and segmental glomerulosclerosis, resembling renal lesions in humans like oligomeganephronia, membranous nephropathy, minimal change nephritis, proliferative glomerulonephritis, analgesic nephropathy, diabetes mellitus, unilateral nephrectomy, cortical necrosis, and unilateral renal agenesis (9).

EXAMPLE 3

Measurement of Urine Protein Excretion and Treatment with Des-Asp-Angiotensin I Following the operation, each animal was placed in a metabolic cage for 24 hours once a week for a duration of 8 weeks. The 24-hour urine output and the concentration of protein in the urine were measured. After the 8$^{th}$ week, the animals were randomly divided into two groups (8 animals per group). Animals in one of the group (the treatment group) were orally administered 762 nmoles/kg/day of des-Asp-angiotensin I dissolved in 0.5 ml of saline via a 1-ml syringe with a blunted needle for a period of 8 weeks. The dose of 762 nmoles/kg/day was calculated based on the maximum effective oral anti-cardiac hypertrophic dose (250 nmole per rat of average weight of 328 g) in the original parent patent. Animals in the other group (the control group) were similarly administered with 0.5 ml of saline. Weekly measurement of 24-hour urine output and the concentration of protein in the urine in these animals were carried out for another 8 weeks. The protocol was designed based on our preliminary observation that urinary excretion of protein in the ⅚ nephrectomized rats commenced to increase above the normal value in 7th to 8th week post nephrectomy. A repeat of the experiment with 12 nephrectomized rats per group was carried out.

To study the effect of des-Asp-angiotensin I on normal rats per se, one group of normal rats (12 animals) were treated with saline and another 12 normal rats treated with 762 nmoles/kg/day. Their once a week 24-hour urine output and urine protein concentration were similarly measured.

EXAMPLE 4

Effect of des-Asp-Angiotensin

The results of the study are summarized in Table 2, Table 3 and Table 4. Data were expressed as mean±SEM. Significant differences were determined by one way ANOVA and post hoc Newman Kleuf test. The accepted level of significance was p<0.05. Des-Asp-angiotensin I is an effective agent in attenuating the progressive development of proteinuria in ablation nephropathic rats. The anti-proteinuric action is brought about by an oral dose of 762 nmoles/kg/day. At this oral dose, the nonapeptide had no effect on the urinary excretion of protein in normal rats.

TABLE 2

Effects of des-Asp-angiotensin I on proteinuria in rats

| Animal Groups | 24-hour urinary excretion of protein (mg) | |
| --- | --- | --- |
| | Weeks 1-8 | Weeks 9-16 |
| Ablation proteinuric rats (control group) | 18.7 ± 2.8 | 37.2 ± 2.3 |
| Ablation proteinuric rats (treatment group) | 16.4 ± 1.6 | *28.7 ± 2.5 |

Values were mean ± SEM obtained from 8 individual rats.
*Significantly different (p = 0.024) from the corresponding value of the control group.

TABLE 3

Effects of des-Asp-angiotensin I on proteinuria in rats

| Animal Groups | 24-hour urinary excretion of protein (mg) | |
| --- | --- | --- |
| | Weeks 1-8 | Weeks 9-16 |
| Ablation proteinuric rats (control group) | 19.5 ± 1.9 | 51.7 ± 4.7 |
| Ablation proteinuric rats (treatment group) | 19.9 ± 1.5 | *39.6 ± 3.3 |

Values were mean ± SEM obtained from 12 individual rats.
*Significantly different (p = 0.048) from the corresponding value of the control group.

TABLE 4

Effects of des-Asp-angiotensin I on urinary protein excretion in normal rats

| Animal Groups | 24-hour urinary excretion of protein (mg) | |
| --- | --- | --- |
| | Weeks 1-8 | Weeks 9-16 |
| Normal rats (control group) | 18.7 ± 1.8 | 19.9 ± 2.2 |
| Normal rats (treatment group) | 16.1 ± 1.7 | 17.8 ± 1.1 |

Values were mean ± SEM obtained from 12 individual rats.

BIBLIOGRAPHY

1. Blair-West et al. (1971) *J. Clin. Endocrinol. Metab.* 32:275
2. Tsai et al. (1975) *J. Med. Chem.* 18:1180
3. Sim and Chai (1996) *Br J. Pharmacol.* 117:1504
4. Sim and Radhakrishnan (1997) *Eur. J. Pharmacol.* 257:R1
5. Sim and Min (1998) *Int. J. Cardiol.* 63:223-227
6. Hamar et al. (1999) *J. Am. Soc. Nephrol.* IV:S234
7. Nakamura et al. (1996) *Kidney Int.* 55:5109
8. Kettler et al. (1996) *Ann. Rev. Physiol.* 57:279
9. Strauch and Gretz (1988) *Contr. Nephrol.* 60:1-8
10. Sambrook et al. (1989). Cloning. A laboratory manual. Cold Spring Harbour Laboratory, Cold Spring Harbour, N.Y.
11. Morrison (1966) *Meth. Achiev. Exp. Pathol.* 1:455-475, (1966)

We claim:

1. A method for the treatment of a renal-related disorder, wherein the renal-related disorder is focal or segmental glomerulosclerosis, oligomeganephronia, membranous nephropathy, minimal change nephritis, proliferative glomerulonephritis, analgesic nephropathy, unilateral nephrectomy, cortical necrosis or unilateral renal agenesis, said method comprising administering to a subject in need of such treatment an effective amount of des-Asp-angiotensin I, or a single amino acid insertion of des-Asp-angiotensin I, said single amino acid insertion being selected from the 20 naturally occurring amino acids, and said single amino acid insertion being an intra-sequence insertion.

2. A method according to claim 1 wherein the renal-related disorder is glomerulosclerosis.

3. The method according to claim 2 wherein said des-Asp-angiotensin I or said single amino acid insertion of des-Asp-angiotensin I is orally administered.

4. The method according to claim 2 wherein said des-Asp-angiotensin I or said single amino acid insertion of des-Asp-angiotensin I is administered by suppository.

5. The method according to claim 2 wherein said des-Asp-angiotensin I or said single amino acid insertion of des-Asp-angiotensin I is parenterally administered.

6. The method according to claim 2 wherein said des-Asp-angiotensin I or said single amino acid insertion of des-Asp-angiotensin I is administered in the form of a solid dosage.

7. The method according to claim 2 wherein said des-Asp-angiotensin I or said single amino acid insertion of des-Asp-angiotensin I is administered in the form of a liquid dosage.

8. The method according to claim 1 wherein the effective amount is 0.9 mg/kg/day.

* * * * *

UNITED STATES PATENT AND TRADEMARK OFFICE
CERTIFICATE OF CORRECTION

PATENT NO. : 7,553,928 B2
APPLICATION NO. : 10/269458
DATED : June 30, 2009
INVENTOR(S) : Sim et al.

It is certified that error appears in the above-identified patent and that said Letters Patent is hereby corrected as shown below:

In the specification

The following text, beginning at column 2, line 60, is deleted:

"BREIF DESCRIPTION OF THE DRAWINGS

Figure 1:
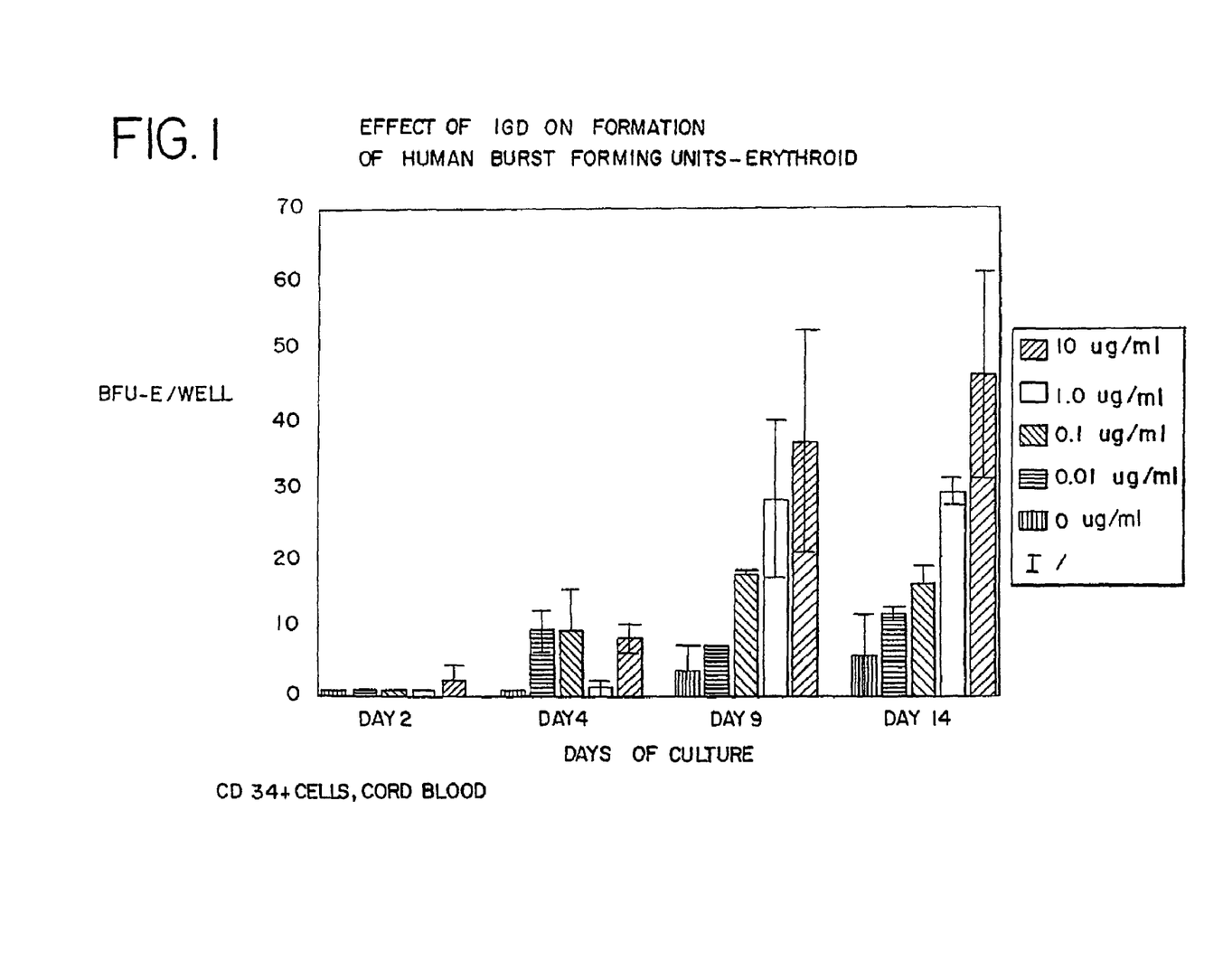
FIG. 1 is a graph showing the effect of IGD on formation of human burst forming units-erythroid.
Figure 2:
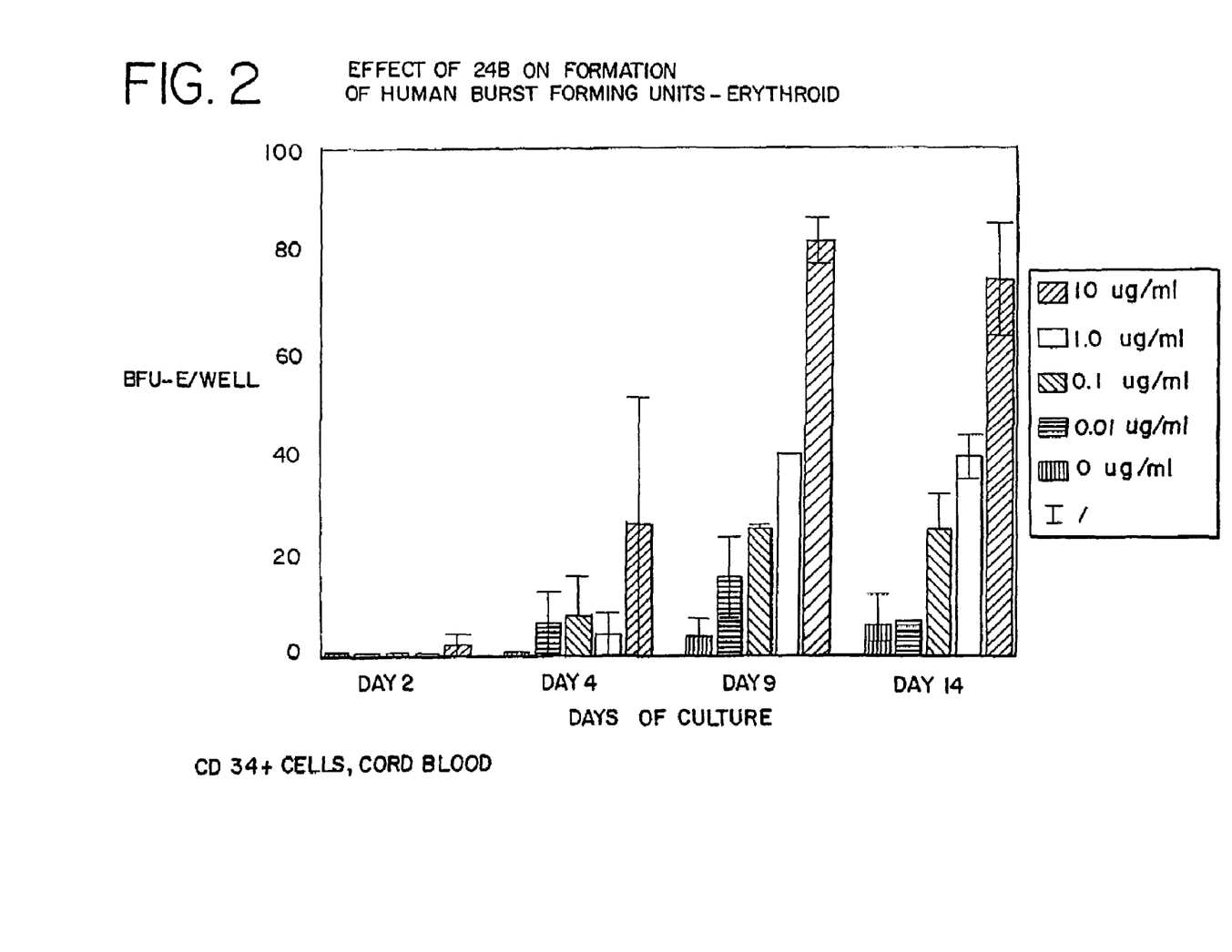
FIG. 2 is a graph showing the effect of 24B on formation of human burst forming units-erythroid.
Figure 3:
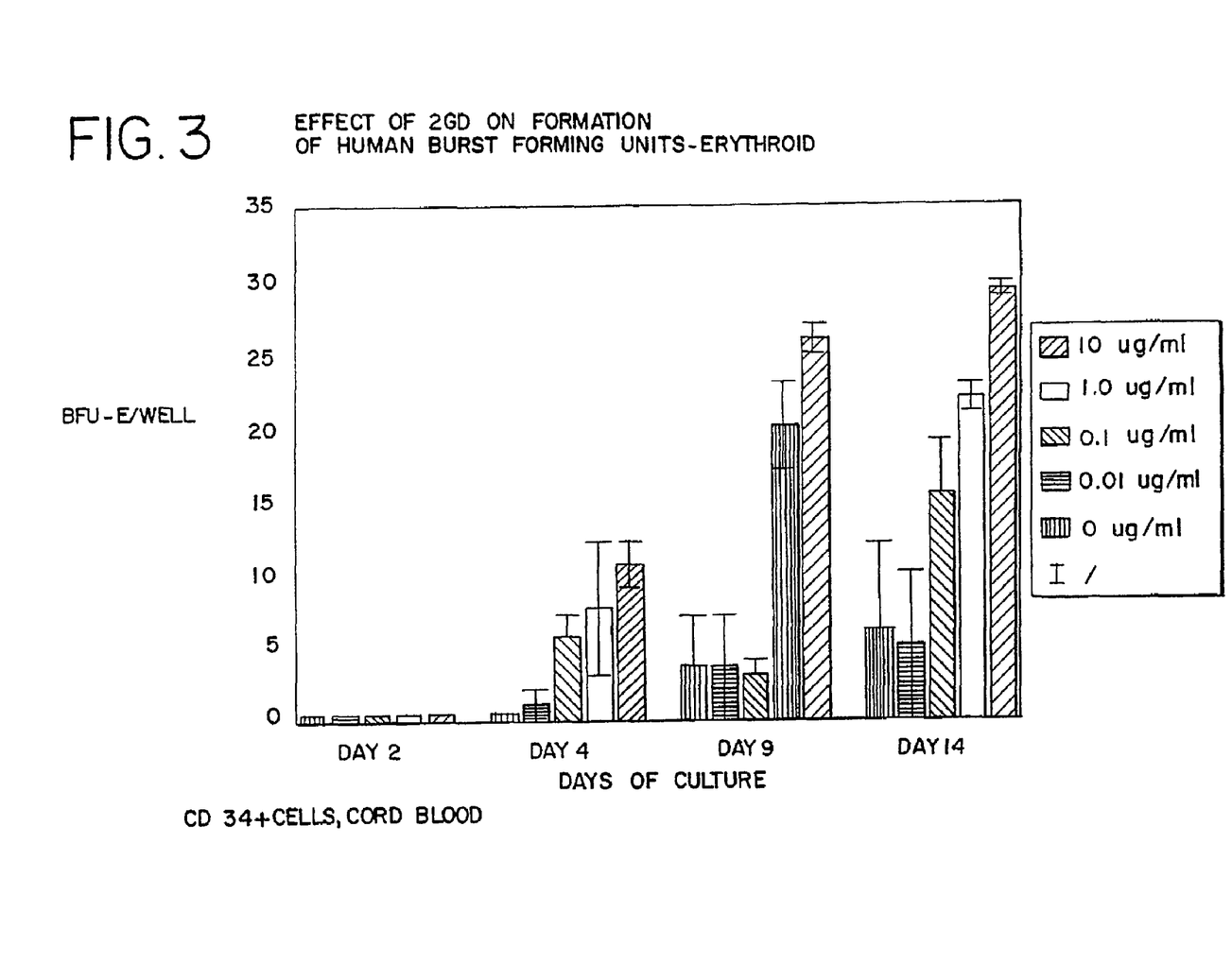
FIG. 3 is a graph showing the effect of 2GD on formation of human burst forming units-erythroid.
Figure 4:
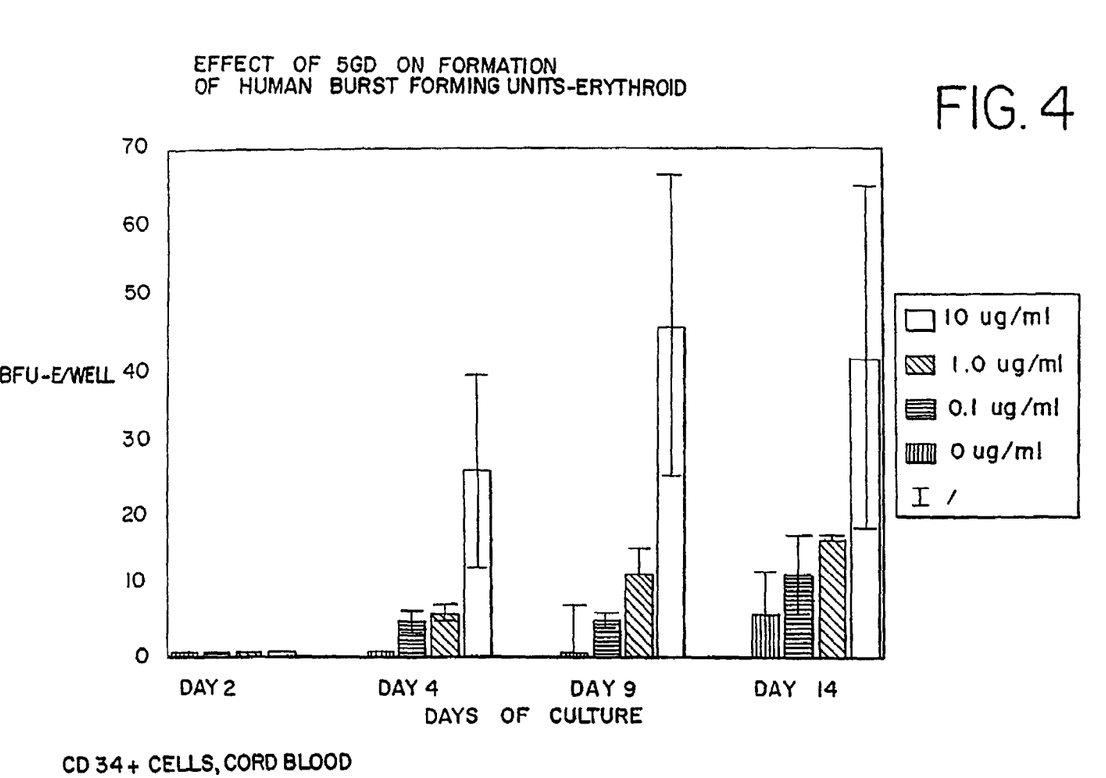
FIG. 4 is a graph showing the effect of 5GD on formation of human burst forming units-erythroid.
Figure 5:
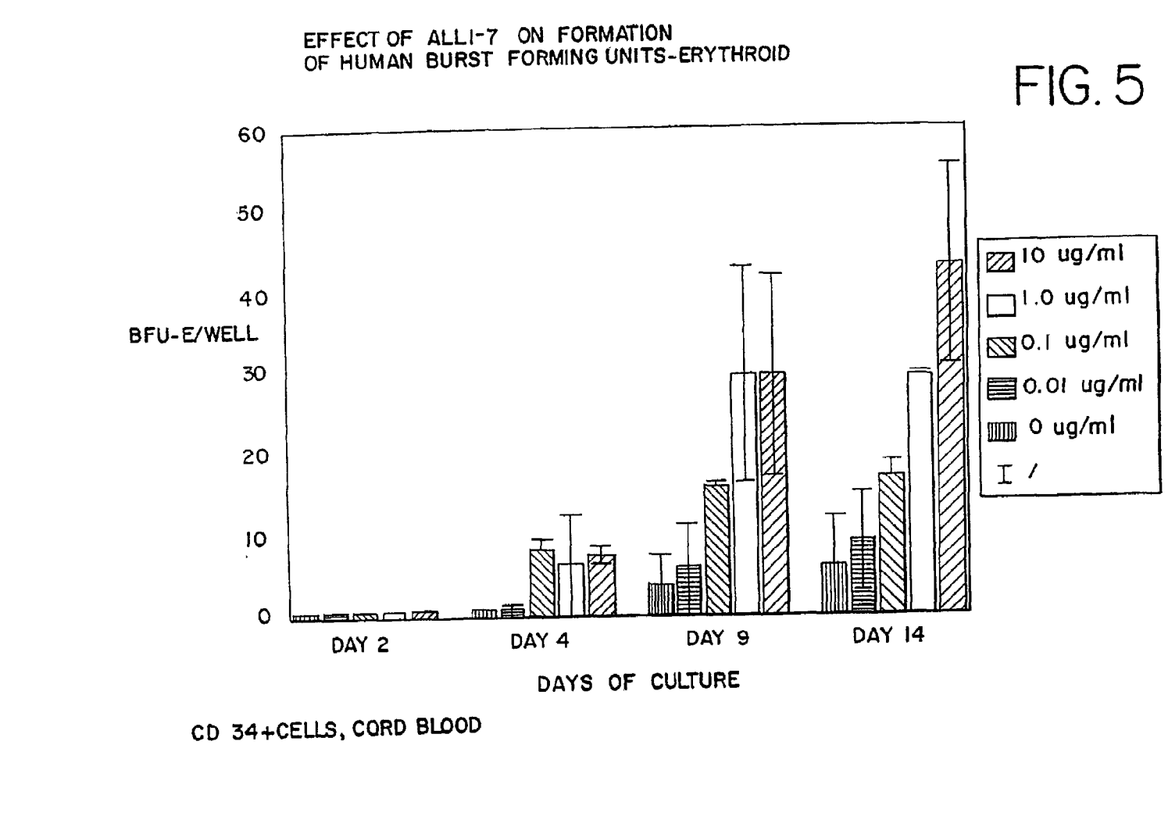
FIG. 5 is a graph showing the effect of ALLI-7 on formation of human burst forming units-erythroid.
Figure 6:
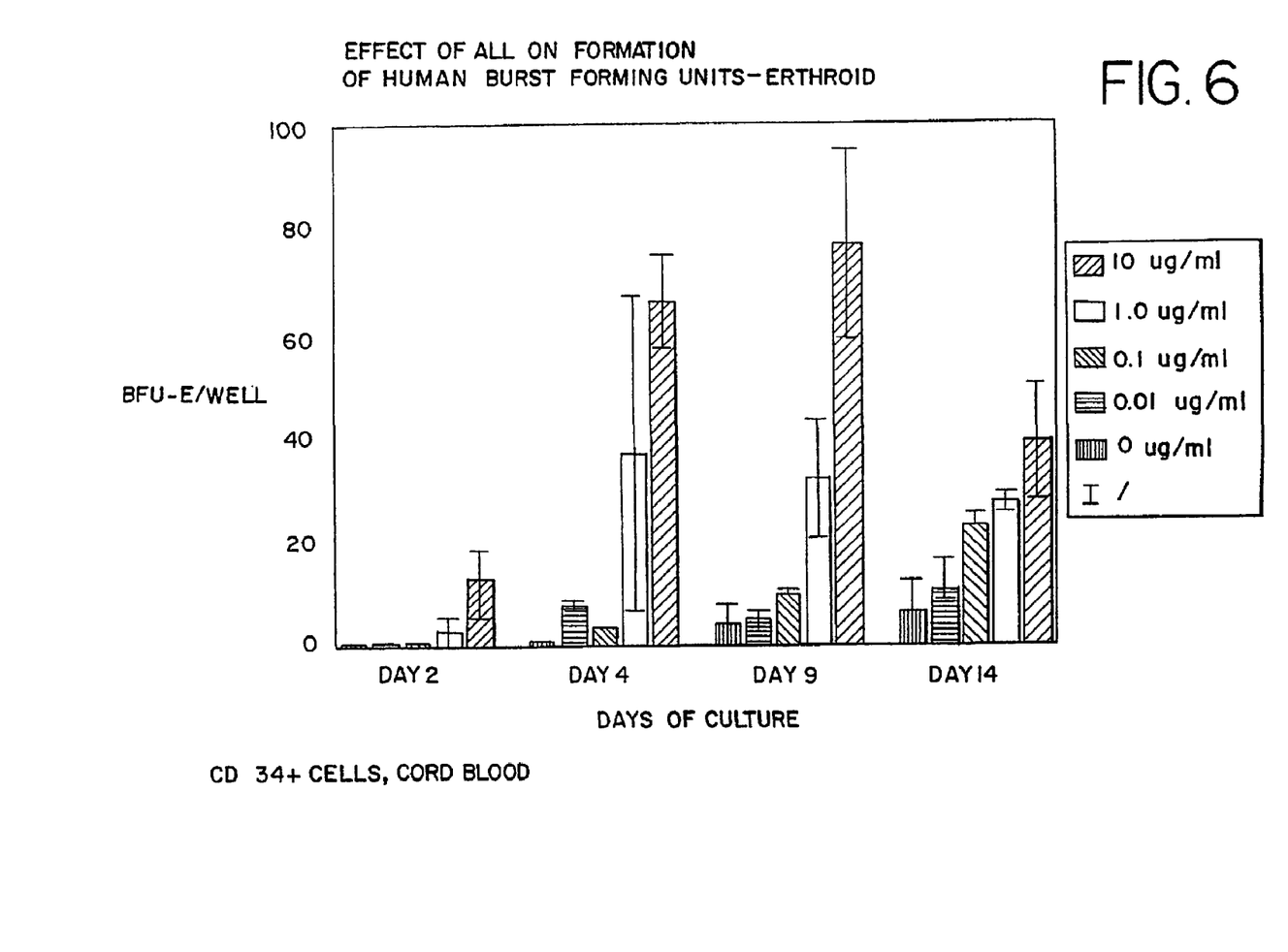
FIG. 6 is a graph showing the effect of all on formation of human burst forming units-erythroid.

FIG. 1 is a graph showing the effect of IGD on formation of human burst forming units-erythroid.
FIG. 2 is a graph showing the effect of 24B on formation of human burst forming units-erythroid.
FIG. 3 is a graph showing the effect of 2GD on formation of human burst forming units-erythroid.
FIG. 4 is a graph showing the effect of 5GD on formation of human burst forming units-erythroid.
FIG. 5 is a graph showing the effect of ALLI-7 on formation of human burst forming units-erythroid.
FIG. 6 is a graph showing the effect of all on formation of human burst forming units-erythroid."

In the drawings

FIGS. 1-6 are deleted.

Signed and Sealed this

Twentieth Day of April, 2010

David J. Kappos
*Director of the United States Patent and Trademark Office*